United States Patent
Smith et al.

(10) Patent No.: US 7,559,916 B2
(45) Date of Patent: Jul. 14, 2009

(54) CATHETER WITH CONTROLLABLE STIFFNESS AND METHOD FOR OPERATING A SELECTIVE STIFFENING CATHETER

(75) Inventors: Kevin W. Smith, Coral Gables, FL (US);
Matthew A. Palmer, Miami, FL (US);
Derek Dee Deville, Miami, FL (US);
Sean M. McBrayer, Miami, FL (US);
Korey Robert Kline, Miami, FL (US)

(73) Assignee: Syntheon, LLC, Miami, FL (US)

( * ) Notice: Subject to any disclaimer, the term of this patent is extended or adjusted under 35 U.S.C. 154(b) by 581 days.

(21) Appl. No.: 11/233,993

(22) Filed: Sep. 23, 2005

(65) Prior Publication Data
US 2006/0069346 A1 Mar. 30, 2006

Related U.S. Application Data

(60) Provisional application No. 60/612,684, filed on Sep. 24, 2004.

(51) Int. Cl.
*A61M 31/00* (2006.01)
(52) U.S. Cl. ................................... 604/95.04
(58) Field of Classification Search .............. 604/95.01, 604/95.02, 95.03, 95.04, 95.05; 606/27, 606/28, 32, 41; 607/96
See application file for complete search history.

(56) References Cited

U.S. PATENT DOCUMENTS

| | | | | | |
|---|---|---|---|---|---|
| 3,359,974 | A | * | 12/1967 | Khalil | 600/526 |
| 4,176,662 | A | * | 12/1979 | Frazer | 600/114 |
| 4,581,390 | A | * | 4/1986 | Flynn | 523/112 |
| 5,143,085 | A | * | 9/1992 | Wilson | 600/585 |
| 6,159,187 | A | * | 12/2000 | Park et al. | 604/264 |
| 6,926,669 | B1 | | 8/2005 | Stewart et al. | |

* cited by examiner

*Primary Examiner*—Manuel A Mendez
(74) *Attorney, Agent, or Firm*—Mayback & Hoffman, P.A.; Gregory L. Mayback; Scott D. Smiley

(57) ABSTRACT

A method and device for treating a Chronic Total Occlusion provides a controllable stiffness catheter with a shaft having a stiffness sheath and an access lumen. The device has a stiffness device in a stiff state below a given temperature and in a soft state above the temperature, a temperature-changing device in thermal contact with the stiffness device, the temperature-changing device changing a temperature of the stiffness device below and above the temperature, and a power controller electrically connected to the stiffness device and selectively supplying power to the temperature-changing device to change a stiffness of the stiffness device between the stiff and soft states. A guidewire is moved to a treatment site and the catheter moves along the guidewire up to CTO in its soft state. The catheter stiffens without straightening and, in the stiff state, the catheter or the guidewire is projecting through the CTO.

35 Claims, 4 Drawing Sheets

CATHETER WITH CONTROLLABLE STIFFNESS AND METHOD FOR OPERATING A SELECTIVE STIFFENING CATHETER

CROSS-REFERENCE TO RELATED APPLICATION

This application claims the priority, under 35 U.S.C. §119, of U.S. Provisional Patent Application No. 60/612,684 filed Sep. 24, 2004, the entire disclosure of which is hereby incorporated herein by reference in its entirety.

STATEMENT REGARDING FEDERALLY SPONSORED RESEARCH OR DEVELOPMENT n/a

FIELD OF THE INVENTION

The invention lies in the field of medical devices, namely, catheters. In particular, the invention relates to catheters that can change stiffness characteristics in use.

BACKGROUND OF THE INVENTION

To gain access to treatment sites in the body, catheters must be flexible enough to conform to and follow natural anatomical pathways as they are advanced. These pathways can be quite tortuous, made of soft and delicate tissues with many twists and turns. In the vasculature, this is especially the case, and even more so in certain areas of the vasculature such as the vessels of the brain and the coronary arteries.

When treating a site in the vasculature, the state-of-the-art practice is to first gain access to the treatment site with a flexible, steerable guidewire. Such a guidewire can be precisely controlled by the physician and steered into place using radiographic guidance. Once the guidewire is in-place, the catheter is advanced over the guidewire. The catheter must be flexible enough to smoothly follow the pathway of guidewire. The catheter can, then, be used to deliver the treatment.

In the case of arterial blockage, the catheter may be a balloon dilatation catheter that is used to open the blockage. The guidewire is, first, passed beyond the lesion, and the catheter is advanced over the guidewire and through the lesion. In the case of complete or nearly complete blockage, the force required to advance the guidewire through the lesion can be difficult for the physician to generate by pushing on the flexible guidewire from the arterial access site. Further, this access site may be far from the treatment site, such as in the case of coronary arterial treatment where access to the coronary arteries is gained though the femoral artery. In such a situation, the physician is trying to advance the flexible guidewire through an obstruction over 100 cm away from where he/she is pushing. The same flexibility that helped gain access to the treatment site now inhibits the advancement of the guidewire. The guidewire bends and buckles under the strain and very little thrust is delivered to the tip of the guidewire.

Current practice advances the balloon catheter up to the treatment site to provide support to the guidewire as it is advanced through the lesion. This is an improvement, but the catheter is also very flexible and provides little if any additional support. Specialty support catheters, which offer more support than balloon catheters, are also used. These provide an improvement over balloon catheters but are also limited by how flexible they must be to reach the treatment site.

The above-mentioned problems are compounded in the case of a total arterial blockage or Chronic Total Occlusion (CTO). Accordingly, most CTOs go untreated. And, there is no catheter-based standard accepted practice for CTO treatment. Currently, treatment of CTOs by catheter interventionalists is performed by attempting to pass a guidewire across the CTO. Once the guidewire is across, a low profile balloon catheter can be advanced over the guidewire to dilate the lesion. Such a procedure is almost always followed by placement of a stent. Specialty guidewires are available to aid the physician in this effort but they, too, are limited in their utility by the constraints of flexibility and compliance. It is noted that attempting to cross CTOs is a tedious practice with current equipment and is met with limited success.

Therefore, it would be beneficial to provide a catheter that can advance up to the treatment site with sufficient flexibility through a tortuous path and that can provide sufficient support to advance through a CTO lesion.

SUMMARY OF THE INVENTION

It is accordingly an object of the invention to provide a catheter with controllable stiffness and method for operating a selective stiffening catheter that overcome the hereinafore-mentioned disadvantages of the heretofore-known devices and methods of this general type and that can traverse a natural passage of the body in a first flexible state and can be made to change to a second stiffer state and cycle back and forth repeatedly between these states at will and that can traverse tortuous anatomy by conforming to it and, once in-place, can be made to stiffen and maintain its tortuous shape in the anatomy.

The catheter of the present invention provides a platform on which physicians can deliver tools to treatment sites to aid in the crossing of arterial blockages, especially, CTOs. In the stiff state, these tools can be used and the force applied by the tools on the treatment site can be enhanced and increased based upon the stiffness properties of the catheter.

The catheter according to the invention has a stiffness that can be controlled during use. The stiffness of the catheter can be changed during use from soft and flexible to firm and stiff and back again, if desired. The entire length of the catheter can be made to change its stiffness characteristics. Alternatively, and/or additionally, any portion or portions of the device can be configured to change its stiffness characteristics as well.

The catheter is delivered to the treatment site in the flexible state, in which, it will track over the guidewire and conform to the anatomical pathway, e.g., the vasculature. Once in-place, the catheter can be made to become stiff (either in whole or in part) without straightening and, thereby, maintain its conformance to the vasculature. In such a state, the catheter provides a stiff conduit to deliver tools to the treatment site without compromising the natural anatomy. This stiffness provides the support necessary to efficiently advance the guide or crossing wires without loss of motion and efficiently transmit thrust loads to the tools.

In the case of a guidewire as described above, the guidewire will, with use of the catheter according to the invention, not flex away from the treatment site when pushed and provides great increases in feel, control, and thrust. Such characteristics aid in the successful crossing of difficult-to-cross lesions and provide an opportunity to cross CTOs.

The vasculature example above has been used to describe the problem and embodiments of the present invention, but it can be appreciated that this same concept can be used in any part of the body.

With the foregoing and other objects in view, there is provided, in accordance with the invention, a controllable stiffness catheter, including a shaft having a stiffness sheath and an access lumen, a stiffness device having a heater and a melting binder in thermal contact with the heater, the stiffness device being disposed in the stiffness sheath, the binder having a transition temperature, being substantially solid at body temperature and softening as the heater warms the binder above the transition temperature, a first electrical conductor electrically contacting the stiffness device, a second electrical conductor electrically contacting the stiffness device and being electrically isolated from the first electrical conductor, a power supply for supplying power, a controller electrically connected to the first electrical conductor, to the second electrical conductor, and to the power supply to form an electrically resistive circuit having the stiffness device as a resistor of the circuit, the controller controlling power supplied to the stiffness device through the circuit and, thereby, controlling a temperature of the heater and the binder, and the stiffness device changes a stiffness of the stiffness sheath between a relatively stiff state when the heater is not energized by the controller and a relatively soft state when the heater is energized by the controller.

With the objects of the invention in view, there is also provided a controllable stiffness catheter, including a shaft having a stiffness sheath and an access lumen, a stiffness device having a heater and a melting binder in thermal contact with the heater, the stiffness device being disposed in the stiffness sheath, the binder having a transition temperature and being substantially solid at body temperature and softening as the heater warms the binder above the transition temperature, and a power controller electrically connected to the heater and selectively supplying power to the heater to change a stiffness of the stiffness sheath between a relatively stiff state when the heater is not powered by the power controller and a relatively soft state when the heater is powered by the power controller.

With the objects of the invention in view, there is also provided a controllable stiffness catheter, including a shaft having a stiffness sheath and an access lumen, means for controlling stiffness disposed in the stiffness sheath, the stiffness controlling means being substantially solid at body temperature and softening above body temperature, and means for supplying heat to the stiffness controlling means to change a stiffness of the stiffness sheath between a relatively stiff state and a relatively soft state. In one embodiment, the stiffness-controlling means is in the stiff state when the heat-supplying means is not activated and the heat-supplying means changes a stiffness of the stiffness sheath to the soft state when the stiffness controlling means is activated.

With the objects of the invention in view, there is also provided a controllable stiffness catheter, including a shaft having a stiffness sheath and an access lumen, a stiffness device disposed at the stiffness sheath and being in a relatively stiff state at or below a first temperature and being in a relatively soft state at or above a second temperature, a temperature-changing device in thermal contact with the stiffness device, the temperature-changing device changing a temperature of the stiffness device at least below the first temperature and above the second temperature, and a power controller electrically connected to the stiffness device and selectively supplying power to the temperature-changing device to change a stiffness of the stiffness device between the stiff state and the soft state.

With the objects of the invention in view, there is also provided a method for manufacturing a controllable stiffness catheter, includes the steps of providing a shaft with a stiffness sheath and an access lumen, disposing a heater inside the stiffness sheath, filling the stiffness sheath containing the heater with a binder to at least partially surround and thermally contact the heater, the binder being substantially solid at body temperature and softening above body temperature, and selectively supplying power to the heater to change a stiffness of the stiffness sheath between a relatively stiff state when the heater is not powered and a relatively flexible state when the heater is powered.

With the objects of the invention in view, there is also provided a method for treating a Chronic Total Occlusion, including the steps of extending a guidewire to a CTO treatment site in a body, providing a controllable stiffness catheter according to claim 39 and, with supplying power to the heater, threading the catheter along the guidewire up to the CTO, removing power from the heater to change stiffness of the stiffness sheath to the stiff state without straightening the catheter, and projecting the guidewire through the CTO. Preferably, the guidewire is a flexible, steerable guidewire.

With the objects of the invention in view, there is also provided a method for operating a selective stiffening catheter, including the steps of placing a selective stiffening catheter in a relatively flexible state, traversing a natural passage of the body with the catheter in the flexible state, and changing the catheter to a relatively stiffer state to substantially maintain a current shape of the catheter in the body.

With the objects of the invention in view, there is also provided a method for treating a Chronic Total Occlusion, including the steps of extending a guidewire to a CTO treatment site in a body, providing a controllable stiffness catheter with a shaft having a stiffness sheath and an access lumen, a stiffness device disposed at the stiffness sheath and being in a relatively stiff state at or below a first temperature and being in a relatively soft state at or above a second temperature, a temperature-changing device in thermal contact with the stiffness device, the temperature-changing device changing a temperature of the stiffness device at least below the first temperature and above the second temperature, and a power controller electrically connected to the stiffness device and selectively supplying power to the temperature-changing device to change a stiffness of the stiffness device between the stiff state and the soft state, threading the catheter along the guidewire up to the CTO in the soft state, changing a stiffness of the stiffness sheath to the stiff state without straightening the catheter, and projecting the guidewire through the CTO.

In accordance with another feature of the invention, the stiffness sheath is of a polymer, in particular, polyurethane, and the access lumen is of a polymer, in particular, PTFE.

In accordance with a further feature of the invention, the access lumen is disposed inside the stiffness sheath and is substantially concentric therewith to define an annulus therebetween. Accordingly, the stiffness device is disposed in the annulus. Preferably, the access lumen has an outer diameter of approximately 0.4 mm and the stiffness sheath has an outer diameter of between approximately 0.4 and 1.73 mm.

In accordance with an added feature of the invention, the stiffness device is disposed between the access lumen and the stiffness sheath. Preferably, the stiffness device is a resistive heating element, in particular, Nickel/Chromium wire.

In accordance with an additional feature of the invention, the binder is a mixture of discontinuous fibers, in particular, the discontinuous fibers are of chopped carbon fiber or glass. The binder is substantially solid up to approximately 105° F. and is soft at or above approximately 115° F.

In accordance with yet another feature of the invention, the stiffness device is one or more carbon fiber tows impregnated with the binder.

In accordance with yet a further feature of the invention, the shaft has a shaft distal end and a shaft proximal end, the power supply and the controller are disposed at the shaft proximal end, the at least one carbon fiber tow has a tow proximal end and a tow distal end, the first electrical conductor has a first distal end electrically connected to the tow distal end and a first proximal end electrically connected to the controller, and the second electrical conductor has a second distal end electrically connected to the tow proximal end and a second proximal end electrically connected to the controller.

In accordance with yet an added feature of the invention, the controller selectively applies a voltage to the first and second electrical conductors to cause current to flow through the circuit and resistively heat the at least one carbon fiber tow and to remove current flowing through the circuit and cool the at least one carbon fiber tow. The heated carbon fiber tow melts and softens the binder to allow individual carbon fibers of the tow to move with respect to each other and, thereby, increase flexibility of the shaft. A third electrical conductor having a distal end electrically connected to an intermediate point of the carbon fiber tow and a proximal end electrically connected to the controller. The controller selectively heats at least one portion of the carbon fiber tow dependent upon current supplied to at least two of the first, second, and third conductors.

In accordance with yet an additional feature of the invention, the heater is located only at a portion of the stiffness sheath. The portion can be a distal portion of the stiffness sheath. Alternatively, the stiffness device can be present throughout an entire length of the stiffness sheath.

In accordance with again another feature of the invention, the stiffness device is disposed between the access lumen and the stiffness sheath and the carbon fiber tow substantially surrounds the access lumen. Preferably, there are more than one carbon fiber tows. The tows can helically surround the access lumen and/or be braided around the access lumen.

In accordance with again a further feature of the invention, the binder is a low-melt-point wax, for example, paraffin, microcrystalline, or blended wax.

In accordance with again an added feature of the invention, the electrical conductors can be of copper wire.

In accordance with again an additional feature of the invention, one of the first and second electrical conductors electrically contact a distal end of heater and runs from the distal end of the catheter to the proximal end of the catheter and another of the first and second electrical conductors electrically contact a proximal end of heater.

In accordance with still another feature of the invention, the power supply is one of a battery and an electric mains.

In accordance with still a further feature of the invention, the controller limits heating of the binder by limiting current through the circuit. The controller includes a Proportional-Integral-Derivative current-sensing controller to limit at current supplied in the circuit. The controller includes a thermocouple for monitoring and regulating a temperature of the binder.

In accordance with still an added mode of the invention, power is supplied to the heater to change stiffness of the stiffness sheath to the soft state, the catheter is withdrawn from the guidewire while leaving the guidewire in the CTO, a balloon catheter is advanced over the guidewire and through the CTO, the balloon catheter having a stent surrounding a balloon, and the balloon is expanded to dilate the CTO and place the stent within the dilated CTO.

In accordance with still an additional mode of the invention, the projecting step is carried out by entirely withdrawing the guidewire from the catheter and replacing the guidewire with a CTO-opening tool having a relatively sharp distal end and the projecting step is carried out by opening the CTO with the CTO-opening tool.

In accordance with another mode of the invention, access to the treatment site is gained with the guidewire by steering the guidewire into place using radiographic guidance.

In accordance with a further mode of the invention, power is applying to the heater to place the catheter in the soft state, a natural passage of a body is traversed with the catheter in the soft state to deliver the catheter to a treatment site, and power is removed from the heater to harden the catheter into the stiff state and to substantially maintain a current shape of the catheter in the body.

In accordance with an added mode of the invention, a guidewire is first placed in the passage of the body to the treatment site and then the applying, traversing, and removing steps are carried out by traversing the passage with the catheter threaded on the guidewire.

In accordance with an additional mode of the invention, the removing step is carried out without straightening the catheter.

In accordance with a concomitant mode of the invention, in the stiff state, the catheter is provided as a relatively stiff conduit to deliver tools to the treatment site without compromising the natural anatomy, to support the tools and efficiently advance the tools therethrough without loss of motion, and to transmit thrust loads to the tools.

Other features that are considered as characteristic for the invention are set forth in the appended claims.

Although the invention is illustrated and described herein as embodied in a catheter with controllable stiffness and method for operating a selective stiffening catheter, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

Advantages of embodiments the present invention will be apparent from the following detailed description of the preferred embodiments thereof, which description should be considered in conjunction with the accompanying drawings in which.

DETAILED DESCRIPTION OF THE PREFERRED EMBODIMENTS

Figure 1:
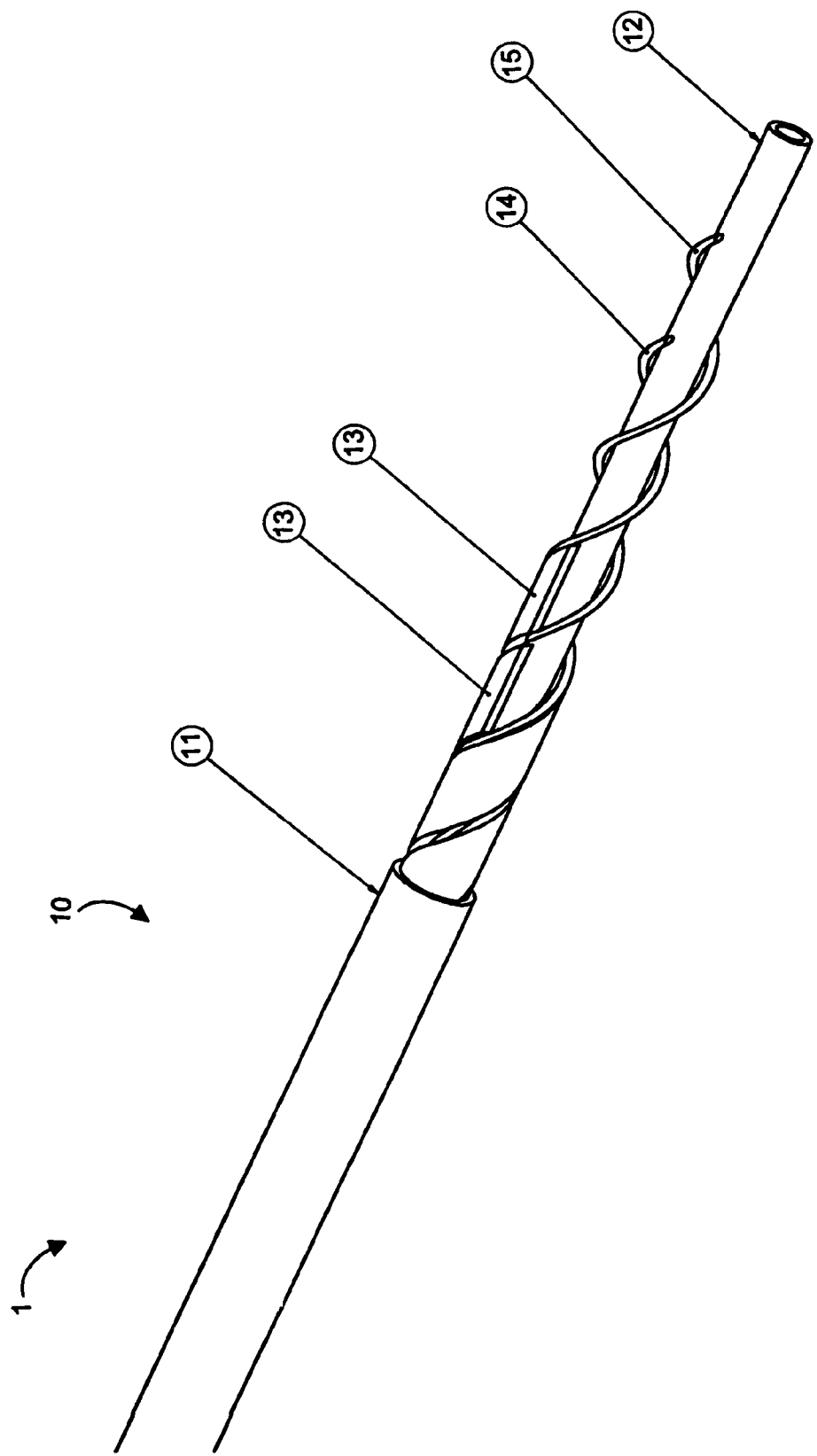
FIG. 1 is a fragmentary, enlarged perspective view of a distal end of a shaft of a catheter according to the invention.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

While the specification concludes with claims defining the features of the invention that are regarded as novel, it is believed that the invention will be better understood from a consideration of the following description in conjunction with the drawing figures, in which like reference numerals are carried forward.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

Referring now to the figures of the drawings in detail and first, particularly to FIG. 1 thereof, there is shown a distal portion of a shaft 10 of an exemplary embodiment of a catheter 1 according to the invention. The shaft 10 is configured with an outer sheath 11 made of a polymer tube such as polyurethane and an inner sheath 12 made of a polymer tube such as PTFE. The inner sheath 12 is assembled substantially concentrically with the outer sheath 11. The annulus between the inner and outer sheaths 12, 11 is filled with a stiffness device, in particular, at least one carbon fiber tow 13 (preferably, 2 to 4 tows 13 extending longitudinally in a helix or braided) impregnated with a binder such as a low-melt-point paraffin or microcrystalline wax or other temperature dependent phase change material. At body temperature, the binder is a solid and, therefore, the carbon fiber tow 13 behaves substantially as a solid carbon fiber rod. (As used herein, "body temperature" is defined to be approximately 40.5° C. (105° F.) or below). In such a condition, the catheter is stiff due the high modulus of the carbon fibers.

It is noted that concentricity is not a requirement. In another exemplary embodiment of the catheter 1 of the present invention, the inner sheath 12 can merely be off-center or the inner sheath 12 can be disposed at the inner wall of the outer sheath 11. In the latter orientation, the space in which the stiffness device resides is somewhat crescent-shaped.

Figure 2:
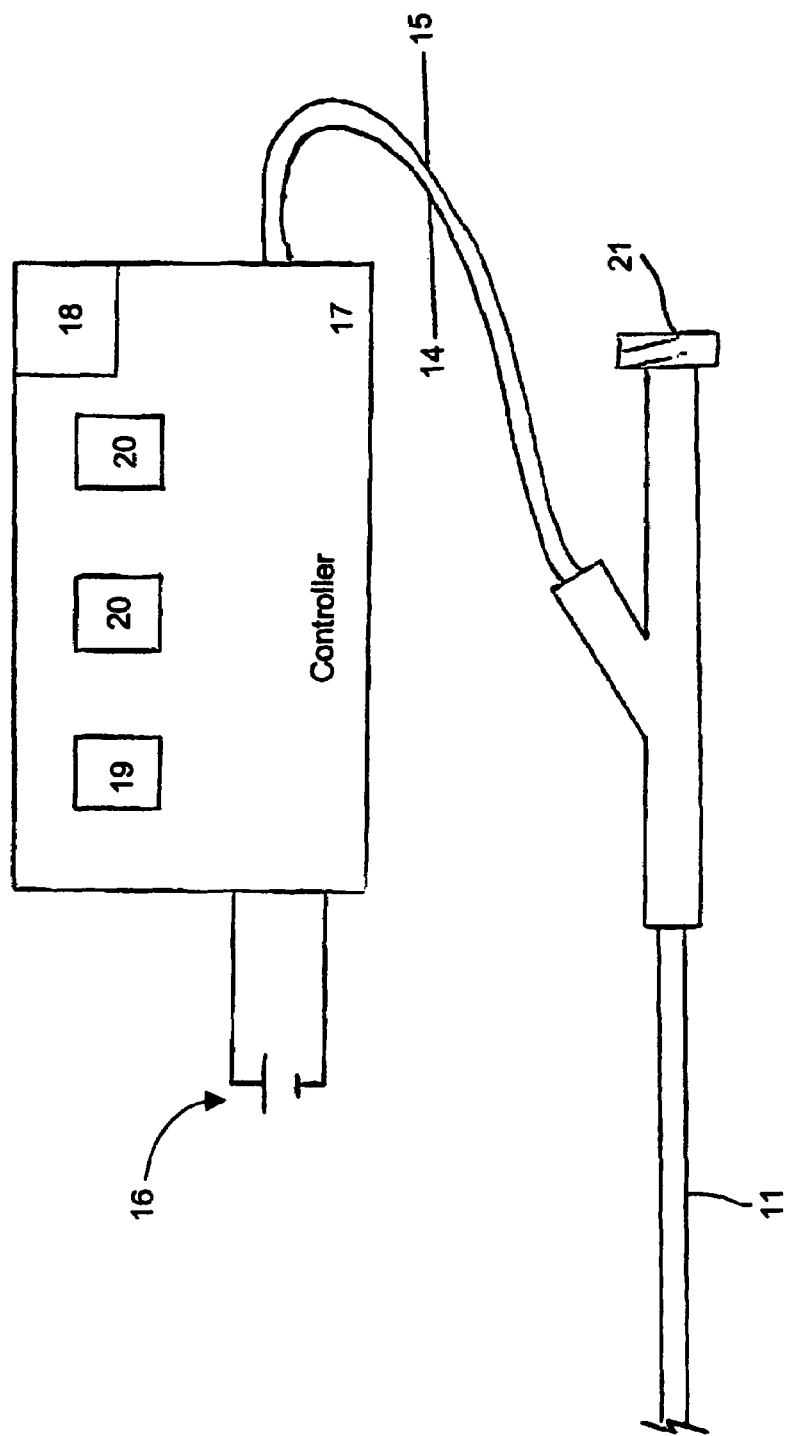
FIG. 2 is a block and schematic circuit diagram and a diagrammatic side elevational view of a proximal end of the catheter according to the invention.

In one exemplary embodiment, an electrical conductor 14, such as insulated copper wire, makes electrical contact with the distal end(s) of the carbon fiber tow(s) 13 and runs from the distal end of the catheter 1 to the proximal end of the catheter 1. The proximal end(s) of the carbon fiber tow(s) 13 makes contact with a second electrical conductor 15, such as copper wire, which extends to the proximal end of the catheter 1 at which resides a power supply 16 (e.g., a battery or an electric mains) and a controller 17 as shown in FIG. 2. The proximal ends of the two conductors 14, 15 are electrically connected to the power supply 16 through the controller 17. These features make up a simple electrical circuit with the carbon fiber tow(s) acting like a resistor in the circuit. When voltage is applied to the two electrical conductors 14, 15, current flows through the circuit 13, 14, 15 and resistively heats the carbon fiber tow(s) 13. When the tow 13 is heated to raise the temperature of the binder above a binder transition temperature, the binder softens (which can include a partial or a full melt) and allows the individual carbon fibers to move with respect to each other, thereby making the catheter shaft more flexible than before. (As used herein, the binder transition temperature is at or above approximately 46° C. (115° F.).) When the voltage is removed from the circuit 13, 14, 15, the binder cools and solidifies. Thus, the catheter shaft 10 stiffens to its then constrained shape. This heating and cooling can be done repeatedly—making the catheter 1 flexible when navigating through a tortuous path and stiff when placed in a position for use, for example.

Another exemplary embodiment of the catheter 1 according to the invention is similar to that illustrated in FIG. 1 but, instead of a concentric configuration, the shaft 10 is constructed of a first hollow sheath 11 made of a polymer tube such as polyurethane and a second hollow sheath 12 made of a polymer tube such as PTFE. The first sheath 11 is assembled next to and outside of the interior of the second sheath 12 such that a cross-section of the two conduits is shaped like the number eight. The entire core of the second sheath 12, therefore, can be used to house the stiffness device 13.

Electrical power for supplying a voltage or current can be provided, for example, by at least one battery 16. This battery 16 can be connected to the conductors 14, 15 through the controller 17, which is configured to limit heating of the binder by limiting current through the circuit 13, 14, 15. Such current limiting can be achieved by using a Proportional-Integral-Derivative (PID) controller whereby a standard feedback loop measures the "output" of the process and controls the "input", with a goal of maintaining the output at a target value, which is called the "setpoint". Such a current-sensing controller, for example, could make the initial current through the circuit 13, 14, 15 high enough to achieve a rapid melt and, thus, a rapid softening, with a subsequent decrease and leveling in the current to just maintain the melt. A thermocouple 18 can be added to actively monitor temperature of the melt. A control switch 19 and indicator LEDs 20 are added to the handle of the catheter 1 to give control and feedback to the user.

The entire length of the catheter 1 can be controllable in stiffness or just a portion of it can be controlled. In the case of a coronary catheter, the distal 20 cm or so can be controllable. The remainder of the catheter 1 can be constructed to have a stiffness sufficient to deliver the controllable portion to the coronary arteries. In such an embodiment, the stiffness device 13 is only present in the distal quarter of the shaft, for example, and one conductor 14 is electrically connected to the distal end of the stiffness device 13 (located at approximately the distal end of the shaft) and the other conductor 15 is electrically connected to a point on the shaft approximately three-quarters of the way to the distal end of the stiffness device 13.

The connection of conductors 14, 15 need not only be at the two ends of the stiffness device 13. Additional non-illustrated conductors can be electrically connected to different places along a single stiffness device 13 that extends the entire length of the catheter 1 to, thereby, subdivide the stiffness device 13 into different stiffening segments. The proximal ends of each of these additionally conductors are electrically connected to the controller 17. Accordingly, only a portion or a set of portions of the stiffness device 13 can be softened depending upon which conductors are energized. Alternatively, the stiffness device 13 can be a set of tows 13 having different lengths with two conductors connected respectively to each tow.

In any embodiment of the conductors 14, 15 and the stiffness device 13, the conductors should be electrically isolated from one another. Even if one conductor contacts a first end of all of a plurality of stiffness devices 13, the other conductors connected to the second end of each stiffness device must be electrically isolated from one another and the one conductor contacting the first end.

FIG. 1 shows a plurality of carbon tows 13 and distal conductors 14, 15 wound around the inner sheath 12. The pitch and the quantity of the carbon fiber tows 13, and the properties of the binder, can be adjusted to affect the final stiffness of the catheter 1. A stiffer binder or the addition of more carbon fiber would lead to a stiffer catheter and a less stiff binder or the subtraction of carbon fiber would lead to a less stiff catheter. A change in the pitch of the wind along the length of the catheter 1 would also vary the stiffness along its length.

The carbon fiber tows 13 can also be oriented longitudinally as rods without wrapping them around the inner sheath 12. Or, a hollow braid of the carbon fiber tows 13 can be made to surround the inner sheath 12. The distal conductor(s) 14, 15 could be included anywhere along the in the rods or braid if desired.

A luer fitting 21 is located at the proximal end of the catheter 1. This fitting 21 provides access to the central lumen of the catheter, for example, for a CTO-piercing tool. A hemostasis valve can be connected to the fitting 21, for example, while the catheter is in use.

In another embodiment of the stiffness device, a mixture of shorter discontinuous fibers such as chopped carbon fiber or fiberglass and binder can be used instead of impregnated continuous carbon fiber tows 13. In such a case, the fibers would no longer be used as the resistive heating measure. Heating of the binder can be achieved by wrapping the inner sheath 12 with a resistive heating element, such as Nickel/Chromium (e.g., NICHROME®) wire. In such a configuration, the wire passes the current and becomes warm, thus heating the surrounding fiber-loaded binder.

In the case of a coronary version of the catheter, the lumen diameter of the inner sheath is, at a minimum, 0.4064 mm (0.016") to ensure free passage of 0.3556 mm (0.014") diameter steerable coronary guidewires. It is preferred for the outer diameter of the catheter to be no greater than 1.651 mm (0.065") to be compatible with an inner diameter of a standard 6 French coronary guide catheter (minimum inner diameter 1.7272 mm (0.068")). Larger or smaller versions can be constructed to suit specific needs.

Figure 3:
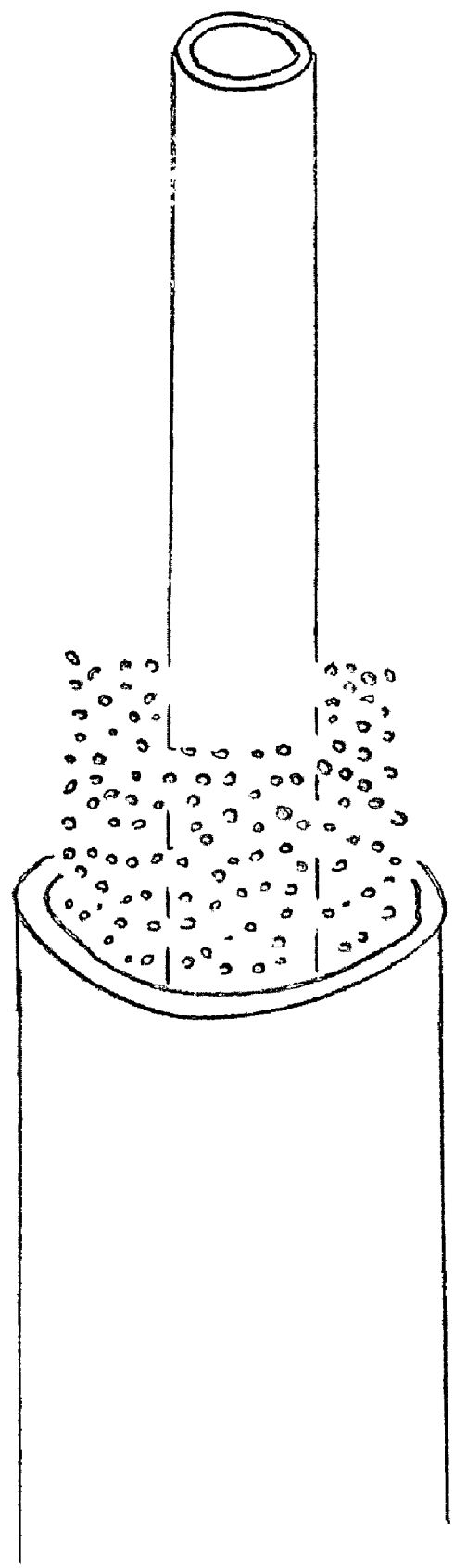
FIG. 3 is a fragmentary, enlarged, cut-away, perspective view of a distal end an alternative embodiment of the catheter according to the invention.
Figure 4:
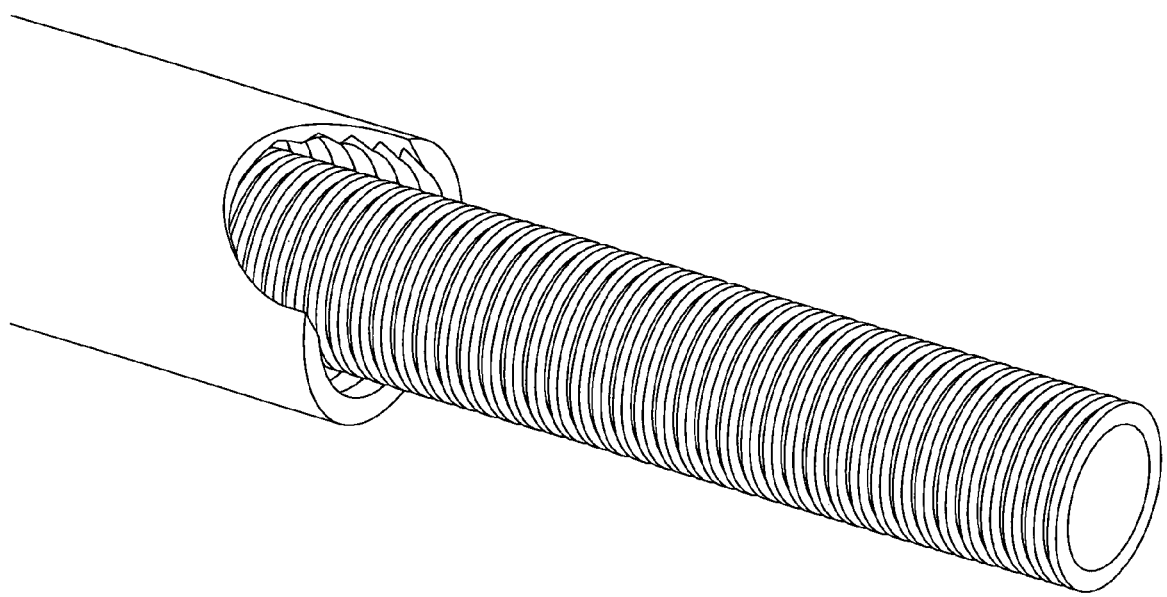
FIG. 4 is a fragmentary, enlarged, cut-away, perspective view of a distal end a further alternative embodiment of the catheter according to the invention.

The catheter can also be stiffened using mechanical measures. The annulus between the inner and outer sheaths can be filled with a fine granular substance, such as aluminum oxide or silica, as shown in FIG. 3. In its flexible state, the fine grains are loose and slide past each other as the catheter is flexed. When vacuum is applied to the annulus, however, the pressure is lowered inside the annulus and the flexible outer sheath begins to compress the grains of the filler together from the urging of the higher pressure outside the catheter. Under such compression, the grains are forced against each other and interlock, no longer sliding past each other and, thus, stiffening the catheter without straightening it. The magnitude of the pressure change between the outside of the catheter and the interior of the annulus affects the catheter stiffness: a small pressure difference (lower vacuum) for a more flexible catheter, a large pressure difference (higher vacuum) for a stiffer catheter. It is clear to see that the catheter could have multiple independent zones that could each be controlled by a different level of vacuum, thus, illustration of this feature is not necessary to understand the present invention. This allows the catheter to be stiff in some zones, and more flexible in others. Such stiffening could also be accomplished without using the granular substance by substituting a rough surface (such as ridges, grooves, bonded grit and combinations thereof) on the outside of the inner sheath and on the inside of the outer sheath as shown in FIG. 4. In its flexible state, the two rough surfaces do not engage each other substantially. When vacuum is applied, the outer sheath is compressed, and the rough surface on the inside of the outer sheath begins to engage the rough surface on the outside of the inner sheath thereby stiffening the catheter.

The following text outlines exemplary procedures for using the catheter 1 of the present invention to pass a CTO.

First, a flexible, steerable guidewire is precisely controlled by the physician and steered into place at a treatment site in a body using, for example, radiographic guidance. Once the guidewire is in place, the catheter 1 of the present invention can be advanced over the guidewire. It is understood that body pathways can be quite tortuous and are made of soft and delicate tissues. This is especially true in the vasculature, in particular, in vessels of the brain and the coronary arteries. Therefore, using the catheter 1 to gain access to the treatment site in the body most likely requires that the catheter 1 start as being flexible to conform to and follow the natural anatomical pathways as it is advanced to the site.

In the case of a CTO, the guidewire is advanced only up to the blockage. Then, the access lumen 12 (whether inside the stiffness lumen 11 or outer sheath 11) is threaded on the guidewire. The catheter 1 is in its softened state or is caused to enter its softened state so that the catheter 1 can be threaded along the guidewire up to the CTO. At the point where the catheter 1 is near the CTO, the catheter 1 is caused to become stiff (without straightening).

In the stiff state, a CTO-opening tool will be used to open the CTO. For example, the CTO-opening tool can be the guidewire itself. Alternatively, a CTO-opening tool can be inserted through the access lumen 12 and into the CTO. If the tool is a device entirely separate from the catheter 1, the guidewire can be removed from the catheter 1 and the CTO-opening tool can be threaded through the access lumen 12. Preferably, the CTO-opening tool is hard (but flexible to traverse the catheter 1) and has a sharp distal end.

The guidewire or tool is pressed through the CTO with the stiffened catheter 1 efficiently transmitting the thrust loads to the tool as the CTO is providing resistance to puncture. Once the guidewire/tool is across the CTO, the guidewire/tool can be used to guide another device that will open and fix the blockage. To remove the catheter 1, first, the catheter 1 is caused to soften. After softening, the catheter 1 is removed and the guidewire/tool is left in the position passed through the CTO. A low profile balloon catheter, for example, is advanced over the guidewire/tool and through the lesion. The balloon is expanded to dilate the lesion. A stent can, then, be placed in the lesion to fix the CTO.

With use of the catheter according to the invention, the guidewire/tool will not flex away from the treatment site when pushed and provides great increases in feel, control, and thrust. Such characteristics aid in the successful crossing of difficult-to-cross lesions and provide an opportunity to cross CTOs.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

We claim:

1. A controllable stiffness catheter, comprising:
a shaft having a stiffness sheath and an access lumen;
a stiffness device having a heater and a melting binder in thermal contact with said heater, said stiffness device being disposed in said stiffness sheath, said binder having a transition temperature, being substantially solid at body temperature and softening as said heater warms said binder above said transition temperature;
a first electrical conductor electrically contacting said stiffness device;
a second electrical conductor electrically contacting said stiffness device and being electrically isolated from said first electrical conductor;
a power supply for supplying power;
a controller electrically connected to said first electrical conductor, to said second electrical conductor, and to said power supply to form an electrically resistive circuit having said stiffness device as a resistor of said circuit, said controller controlling power supplied to said stiffness device through said circuit and, thereby, controlling a temperature of said heater and said binder; and
said stiffness device changes a stiffness of said stiffness sheath between a relatively stiff state when said heater is not energized by said controller and a relatively soft state when said heater is energized by said controller.

2. The catheter according to claim 1, wherein said stiffness sheath is of a polymer.

3. The catheter according to claim 2, wherein said polymer is polyurethane.

4. The catheter according to claim 1, wherein said access lumen is of a polymer.

5. The catheter according to claim 4, wherein said polymer is PTFE.

6. The catheter according to claim 1, wherein said access lumen is disposed inside said stiffness sheath and is substantially concentric therewith to define an annulus therebetween.

7. The catheter according to claim 6, wherein said stiffness device is disposed in said annulus.

8. The catheter according to claim 6, wherein:
said access lumen has an outer diameter of approximately 0.4 mm; and
said stiffness sheath has an outer diameter of between approximately 0.4 mm and approximately 1.73 mm.

9. The catheter according to claim 1, wherein said stiffness device is disposed between said access lumen and said stiffness sheath.

10. The catheter according to claim 1, wherein said stiffness device is a resistive heating element.

11. The catheter according to claim 10, wherein said resistive heating element is Nickel/Chromium wire.

12. The catheter according to claim 1, wherein said binder is a mixture of discontinuous fibers.

13. The catheter according to claim 12, wherein said discontinuous fibers are of chopped carbon fiber or glass.

14. The catheter according to claim 1, wherein said stiffness device is at least one carbon fiber tow impregnated with said binder.

15. The catheter according to claim 14, wherein:
said shaft has a shaft distal end and a shaft proximal end;
said power supply and said controller are disposed at said shaft proximal end;
said at least one carbon fiber tow has a tow proximal end and a tow distal end;
said first electrical conductor has a first distal end electrically connected to said tow distal end and a first proximal end electrically connected to said controller; and
said second electrical conductor has a second distal end electrically connected to said tow proximal end and a second proximal end electrically connected to said controller.

16. The catheter according to claim 15, wherein said controller selectively applies a voltage to said first and second electrical conductors to:
cause current to flow through said circuit and resistively heat said at least one carbon fiber tow; and
remove current flowing through said circuit and cool said at least one carbon fiber tow.

17. The catheter according to claim 16, wherein said heated carbon fiber tow melts and softens said binder to allow individual carbon fibers of said tow to move with respect to each other and, thereby, increase flexibility of said shaft.

18. The catheter according to claim 15, further comprising:
a third electrical conductor having a third distal end electrically connected to an intermediate point of said at least one carbon fiber tow and a third proximal end electrically connected to said controller; and
said controller selectively heating at least one portion of said at least one carbon fiber tow dependent upon current supplied to at least two of said first, second, and third conductors.

19. The catheter according to claim 1, wherein said heater is located only at a portion of said stiffness sheath.

20. The catheter according to claim 19, wherein said portion is a distal portion of said stiffness sheath.

21. The catheter according to claim 1, wherein said stiffness device is present throughout an entire length of said stiffness sheath.

22. The catheter according to claim 14, wherein:
said stiffness device is disposed between said access lumen and said stiffness sheath; and
said at least one carbon fiber tow substantially surrounds said access lumen.

23. The catheter according to claim 22, wherein said at least one carbon fiber tow is a plurality of carbon fiber tows.

24. The catheter according to claim 23, wherein said tows helically surround said access lumen.

25. The catheter according to claim 23, wherein said tows are braided around said access lumen.

26. The catheter according to claim 14, wherein said at least one carbon fiber tow is a plurality of carbon fiber tows.

27. The catheter according to claim 1, wherein said binder is a low-melt-point wax selected from the group consisting of paraffin, microcrystalline, or blended wax.

28. The catheter according to claim 1, wherein said first and second electrical conductors are copper wire.

29. The catheter according to claim 1, wherein one of said first and second electrical conductors electrically contact a distal end of heater and runs from said distal end of the catheter to said proximal end of the catheter and another of said first and second electrical conductors electrically contact a proximal end of heater.

30. The catheter according to claim 1, wherein said power supply is one of a battery and an electric mains.

31. The catheter according to claim 1, wherein said controller limits heating of said binder by limiting current through said circuit.

32. The catheter according to claim 1, wherein said controller limits heating of said heater by limiting current through said circuit.

33. The catheter according to claim 1, wherein said controller includes a Proportional-Integral-Derivative current-sensing controller to limit at current supplied in said circuit.

34. The catheter according to claim 1, wherein said controller includes a thermocouple for monitoring and regulating a temperature of said binder.

35. The catheter according to claim 1, wherein said binder is relatively substantially solid up to approximately 105° F. and is relatively soft at or above approximately 115° F.

* * * * *